United States Patent [19]

Yehl

[11] Patent Number: 5,187,635
[45] Date of Patent: Feb. 16, 1993

[54] SURFACE CLEANING APPARATUS AND METHOD

[75] Inventor: James E. Yehl, Boulder, Colo.

[73] Assignee: American Environmental Systems, Inc., Boulder, Colo.

[21] Appl. No.: 711,951

[22] Filed: Jun. 7, 1991

Related U.S. Application Data

[63] Continuation-in-part of Ser. No. 300,121, Jan. 23, 1989, Pat. No. 5,043,840, which is a continuation-in-part of Ser. No. 138,143, Dec. 28, 1987, Pat. No. 4,911,737.

[51] Int. Cl.$^5$ .............................................. H05F 3/00
[52] U.S. Cl. ..................................... 361/231; 15/1.51; 361/213; 361/229
[58] Field of Search ............... 361/230, 231, 233, 235, 361/212, 213, 227, 228; 15/1.5 R

[56] References Cited

U.S. PATENT DOCUMENTS

| | | | |
|---|---|---|---|
| 2,650,672 | 9/1953 | Barr et al. | |
| 3,711,743 | 1/1973 | Bolasny | 361/231 |
| 4,198,061 | 4/1980 | Dunn | 15/1.5 R |
| 4,377,838 | 3/1983 | Levey et al. | 361/238 |
| 4,745,520 | 5/1988 | Hughey | 361/228 |
| 4,751,759 | 6/1988 | Zoell | 15/1.5 R |
| 4,811,159 | 3/1989 | Foster | 361/231 |
| 4,835,808 | 6/1989 | Hahne et al. | 15/1.5 R |
| 4,911,737 | 3/1990 | Yehl et al. | 361/231 |
| 5,043,840 | 8/1991 | Yehl et al. | 361/231 |

Primary Examiner—Jeffrey A. Gaffin
Attorney, Agent, or Firm—Harold A. Burdick

[57] ABSTRACT

A surface cleaning apparatus and method is disclosed for disbonding, removal and collection of undesired matter from product surfaces, particularly in controlled process environments. The apparatus includes a negatively chargeable staging surface for receipt thereat of a product having a surface or surfaces to be cleaned, a gas stream nozzle having an electron generation source, usually a negative ion source, adjacent to its outlet, and a positive electrostatic field generator having a collector surface spaced from the staging surface. The electrostatic field generator may optionally include pulse generating circuitry for generating pulsations of selected frequency within the positive electrostatic field. Controls are provided for selectively controlling negative charge at the staging surface, ion output, field strength and, when provided, field pulsation frequency.

20 Claims, 4 Drawing Sheets

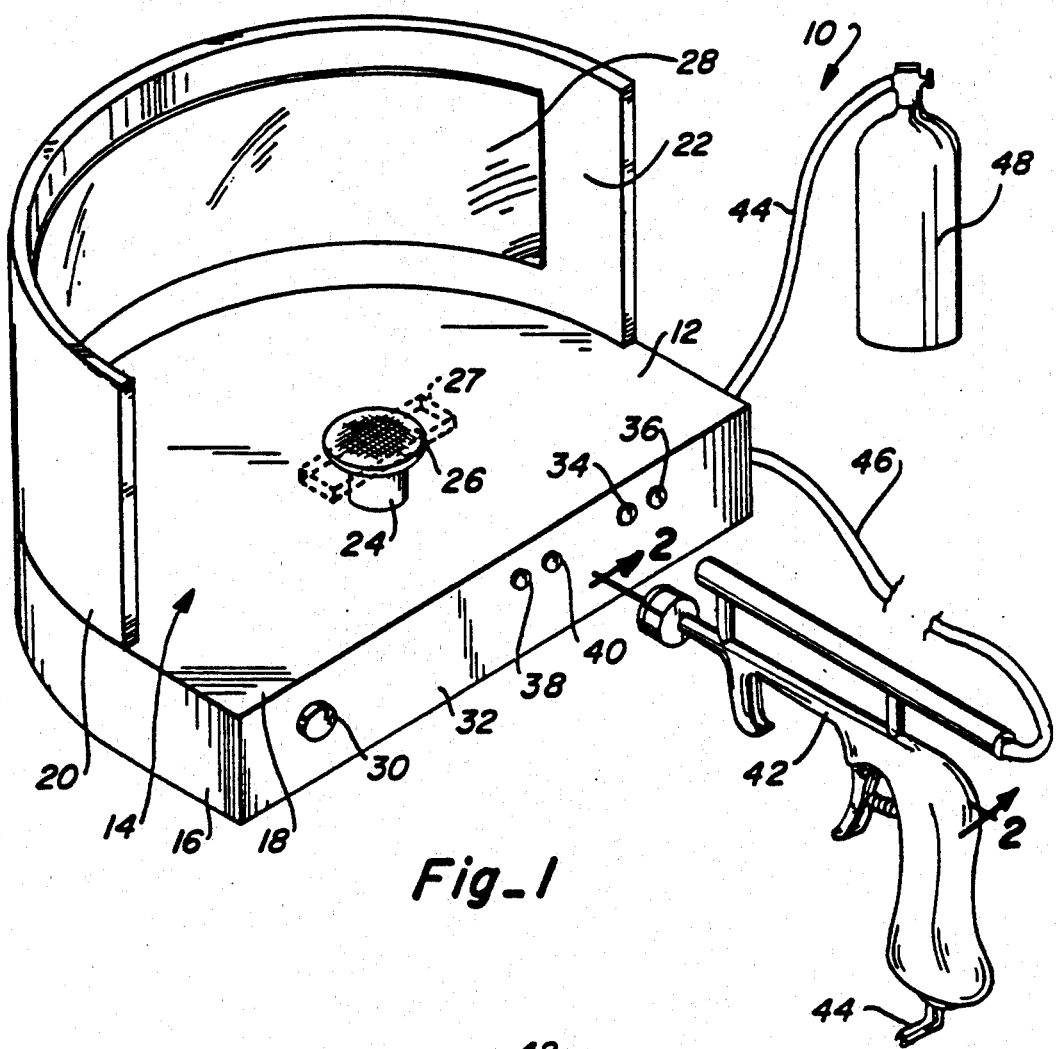
Fig_1
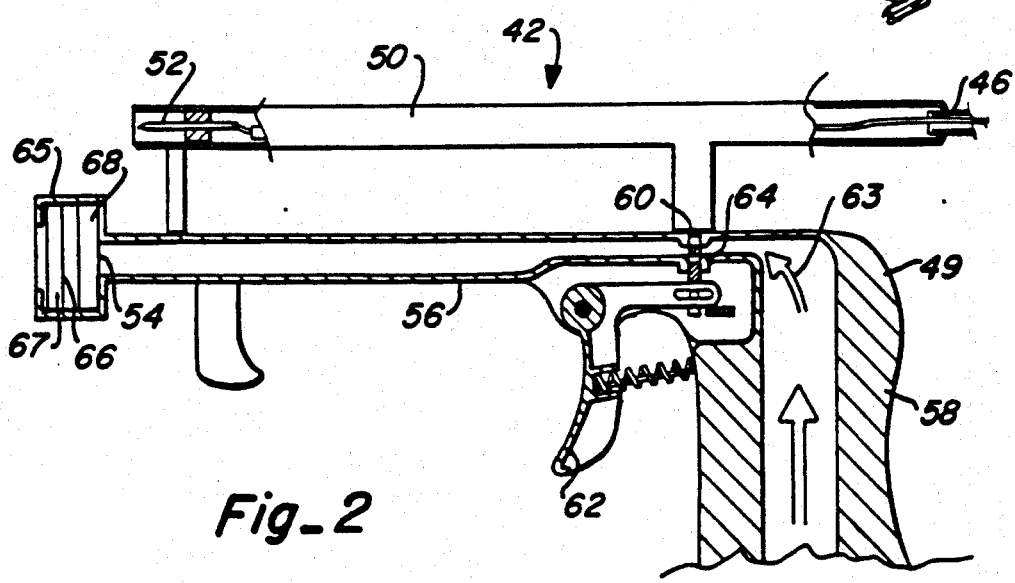
Fig_2

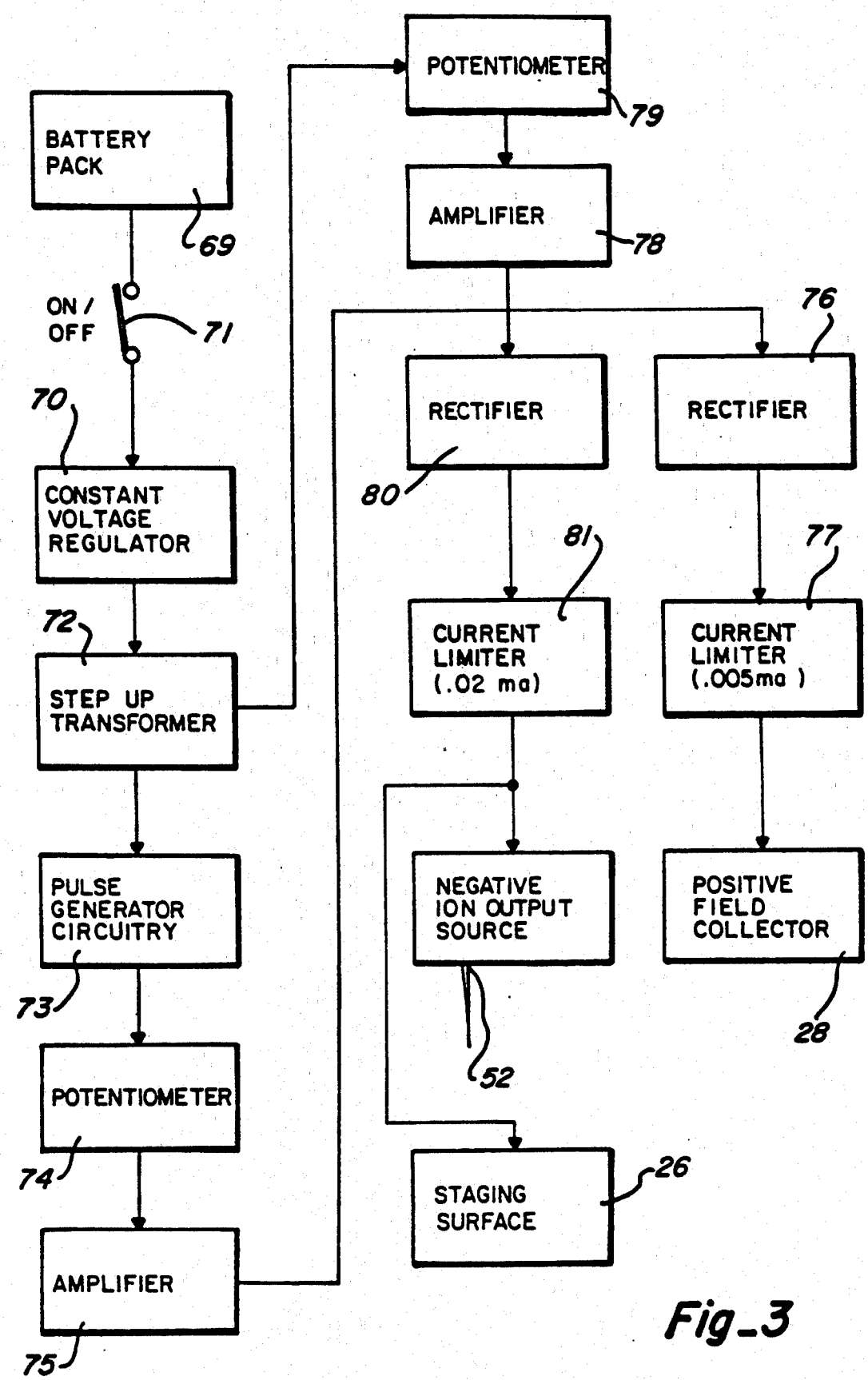
Fig_3

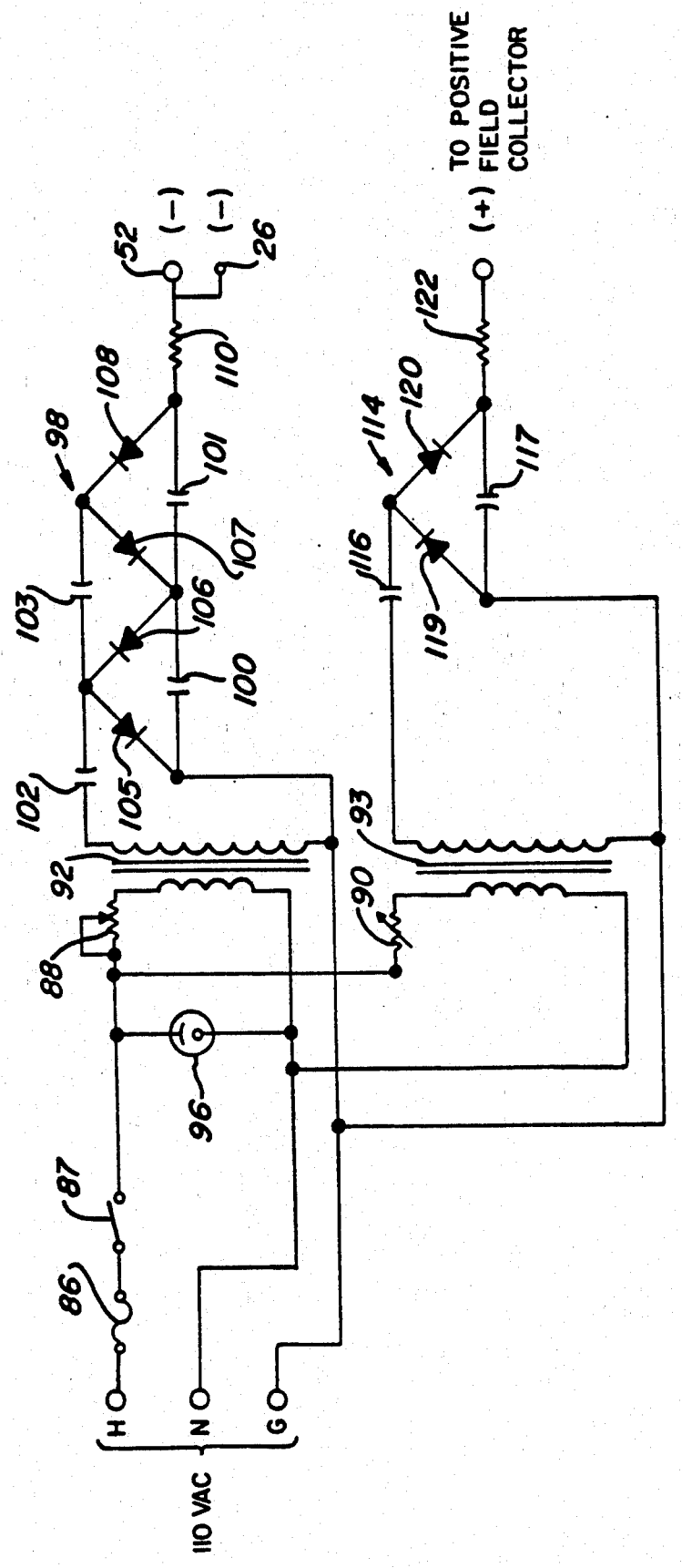

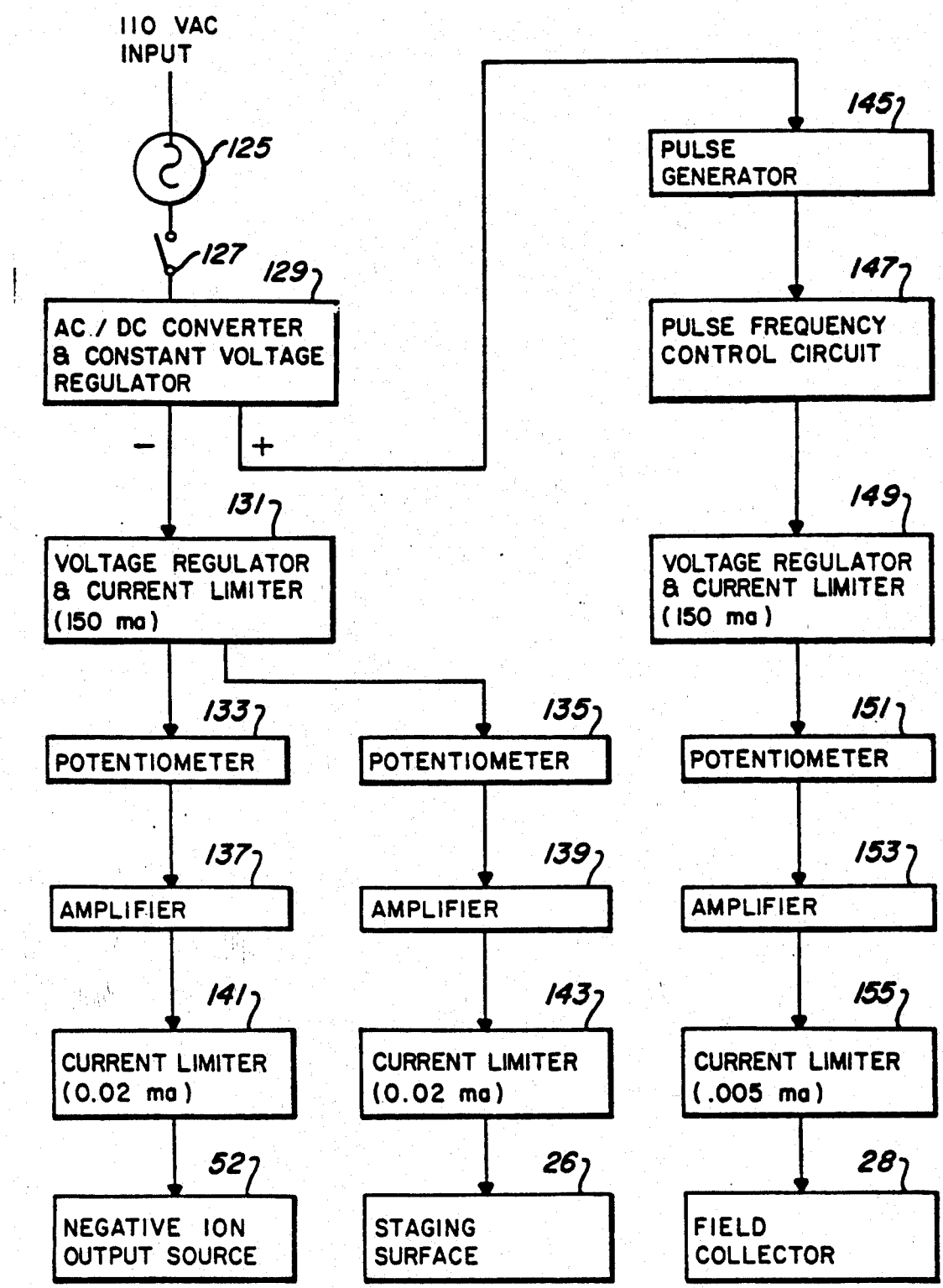
Fig_5

SURFACE CLEANING APPARATUS AND METHOD

RELATED APPLICATION

This application is a continuation-in-part of U.S. Pat. application Ser. No. 300,121 filed Jan. 23, 1989, now U.S. Pat. No. 5,043,840, issued Aug. 27, 1991 and which is a continuation-in-part of U.S. Pat. application Ser. No. 138,143 filed Dec. 28, 1987 and now U.S. Pat. No. 4,911,737 issued Mar. 27, 1990.

FIELD OF THE INVENTION

This invention relates to surface cleaning, and, more particularly, relates to apparatus and methods for removing and collecting contaminants from product surfaces.

BACKGROUND OF THE INVENTION

Devices for ionizing air or air streams for electrostatic dust separation and/or dust collection at a charged collector have been heretofore suggested and/or utilized (see, for example, U.S. Pat. Nos. 2,650,672 and 4,811,159, and German Patent Nos. DE 3201835 A1 and DE 3528590 A1). Surface cleaning devices have also been heretofore suggested and/or utilized which provide for ionization adjacent to a surface to be cleaned, with blowers directed at the surface to dislodge particles, vacuums for suctioning away the dislodged particles being provided adjacent to the surface. Some such devices have included a charged attraction member associated with the vacuum (see U.S. Pat. Nos. 4,835,808, 4,198,061 and 4,751,759).

Such heretofore known devices have not, however, adequately addressed the problem of disbonding particles, including microorganisms, electrostatically held to a product surface, nor have such devices been configured for adaptability for use with a variety of products the surface or surfaces of which are to be cleaned. Further improvement in such devices which addresses the problem of electrostatic bonding, which provides adaptable to a variety of uses, and which avoids undue complexity, for example by elimination of vacuums and the like, could thus still be utilized.

SUMMARY OF THE INVENTION

This invention provides an improved apparatus and method for removal of unwanted matter from product surfaces. The apparatus includes a surface charged at a selected intensity and a preselected polarity, an ion generator for generating a selected quantity of ions of the preselected polarity, and an electrostatic field generator for generating an electrostatic field of selected intensity and having a polarity opposite the polarity of the charged surface and the ions.

The apparatus preferably includes a negatively chargeable platform at a cleaning area, an electron, usually a negative ion, generator, and a positive electrostatic field generator having a collector surface positioned adjacent to the cleaning area. A gas stream outlet, connected with a pressurized gas source, and having an ion output source connected to the ion generator mounted adjacent thereto is provided, the gas stream outlet and ion source preferably being selectively movable relative to the platform. The field generator may optionally include a field pulsator. Controls determine the quantity, or concentration, of ions, the charge intensity at the platform, the intensity of the electrostatic field, and, when provided, the frequency of the pulsations in the electrostatic field.

It is therefore an object of this invention to provide an improved apparatus and method for removal and collection of unwanted matter from, and/or prevention of contamination of, product surfaces.

It is another object of this invention to provide an improved apparatus and method for cleaning product surfaces which is adaptable to a variety of products.

It is another object of this invention to provide an improved apparatus and method for removal of matter from product surfaces which imparts a like to charge a product platform and the matter to be removed to assist disbonding of the matter from the surface.

It is still another object of this invention to provide an improved apparatus and method for cleaning product surfaces which requires no vacuuming of the surfaces to remove unwanted matter therefrom.

It is yet another object of this invention to provide an apparatus for removal of unwanted matter from a product which includes a voltage supply connectable with a voltage source, a surface for receipt of the product thereon and connected with the voltage supply to charge the surface at a preselected polarity, an ion generator for generation of ions of the preselected polarity, and an electrostatic field generator for generating an electrostatic field with a polarity opposite to the preselected polarity, the field generator including a collector spaced from the charged surface.

It is yet another object of this invention to provide an apparatus for cleaning product surfaces which includes a negatively chargeable product receiving platform, a negative ion source, a positive electrostatic field generator having a collector spaced from the platform, and a gas stream outlet connectable with a source of pressurized gas, the platform and collector being mounted on a first mounting structure, and the ion source and gas stream outlet being positioned at a second, selectively movable, mounting structure.

It is still another object of this invention to provide a method for removal of unwanted matter from a product surface which includes the steps of positioning the product on a surface, charging the surface at a preselected polarity, generating ions of the preselected polarity, directing the ions toward the product on the surface, and establishing, at a collector spaced from the product, an electrostatic field having a polarity opposite the preselected polarity.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1 is a perspective view of the apparatus of this invention;

FIG. 2 is a sectional view taken along section lines 2—2 of FIG. 1;

FIG. 3 is a block diagram illustrating a DC powered circuitry for a first embodiment of the apparatus of this invention;

FIG. 4 is a schematic diagram of the components of a second embodiment of the circuitry of the apparatus of this invention; and FIG. 5 is a block diagram illustrating an AC powered circuitry for a third embodiment of the apparatus of this invention.

DESCRIPTION OF THE INVENTION

FIG. 1 illustrates the apparatus of this invention. Apparatus 10 includes mounting structure 12 defining cleaning area 14. Structure 12 includes housing 16 having upper surface 18 and wall 20 having forward face 22. Housing 16 and wall 20 are preferably made of nonconductive material, for example plastic. Wall 20 is preferably an arcuate wall.

Platform 24, having conductive surface 26 at the upper part thereof for receipt of product 27 thereon, is centrally positioned at upper surface 18 of housing 16, and arcuate collector 28 is mounted at forward face 22 of wall 20 (surface 26 and collector 28 being made of any conductive material, for example various metals, electroconductive carbon foam, or the like). The distance between surface 26 and collector 28 in the herein shown embodiment of the device is approximately 12 inches or more (though such relative positioning is not critical to the function of apparatus 10).

On/off control 30 is positioned at front panel 32 of housing 16, as are negative voltage level knob 34 and positive voltage level knob 36. Indicator lights 38 and 40 may be provided to indicate actuation of positive and negative voltage, respectively.

Hand held gas stream/ionization module 42 is connected by flexible supply line 44 and cable 46 to gas source 48 and the circuitry within housing 16, respectively, the line and cable being of a sufficient length to allow a wide range of movement of module 42 for directing the gas stream and ions to cleaning area 14 from a variety of positions and distances. Module 42 (as illustrated best in FIG. 2) includes mounting structure 49 having ionization unit housing 50 mounted thereto with ion source 52 (preferably a point source needle electrode) housed therein and connected by cable 46 to the related circuitry hereinafter described.

Gas stream outlet 54 communicates through channels in barrel 56 and handle 58 of mounting structure 49 and through with supply line 44 pressurized gas source 48 (the gas source being, for example, a pressurized bottle or compressor, the gas preferably being nitrogen, although air or other gases could be utilized). Valve 60 is operated utilizing trigger 62 for opening channel 63 through mounting structure 49 at passageway 64 (FIG. 2 illustrating the valve in its normally closed position).

Outlet 54 includes nozzle 65 having filters 66 therein (for example a 0.3 micron high efficiency particulate air (HEPA) filter 67, and charcoal filter 68).

When ions are generated from point source 52 and valve 60 is opened by pressure against trigger 62, ions are carried in the gas stream in the direction selected by the operator, the pressure applied to trigger 62 controlling the degree of overlap passageway 64 with channel 63 thus controlling both velocity and volume of gas emitted through outlet 54.

Turning now to FIG. 3, one embodiment of a circuitry mounted in housing 16 for control of apparatus 10 is shown, with the apparatus being operable from its own 12 or 24 volt battery pack 69. The DC voltage supplied from battery pack 69 is received by constant voltage regulator 70 upon activation of on/off switching mechanism 71 (controlled at switch control 30 in FIG. 1). Constant voltage regulator 70 (for example a 12 volt Zener diode) provides a steady +12 volt signal which is received by DC step-up transformer 72, the secondary coil of which is center tapped, providing a 350 volt signal at one output and a 2,500 volt signal at the other output. The 350 volt signal may be received by pulse generator 73 (provision of pulsed output is optional) the output signal of which is pulsed at a frequency of about 7.8 Hz. The output is coupled through potentiometer 74 and amplified at 75 (to about 13 KV) and rectified at rectifier 76. The positive portion of the pulsed signal is thereafter received at current limiter 77 for limiting the current of the signal to about 0.02 mA at collector 28.

The 2500 volt signal from step-up transformer 72 is received at amplifier 78 through potentiometer 79 where the signal is amplified providing a 13 KV signal which is rectified at rectifier 80. The negative portion of the signal is received at current limiter 81 (limiting signal current to 0.02 mA) and thereafter at electrode 52 as well as a platform surface 26. Potentiometers 74 and 79 adjust output voltage in a range from 0 to 13.0 KV.

Referring now to FIG. 4, a second embodiment of a circuitry for apparatus 10 is shown for use in association with a conventional 110 volt AC power supply. The 110 volt signal is coupled through fuse 86 and switch 87 to potentiometer 88 and variable resistor 90. Potentiometer 88 is connected to step-up transformer 92 for stepping the voltage up to 1200 volts. Variable resistor 90 is connected to step-up transformer 93 for separately stepping up the voltage output from the secondary coil thereof to 1000 volts. Indicator lamp 96 is provided for indicating operability of the apparatus upon closure of switch 87.

The output from transformer 92 is connected with amplifier and rectifier circuitry 98 for providing a rectified signal therefrom having a user controlled voltage of between 0 and −13 KV. Amplifier and rectifier circuitry 98 includes capacitors 100, 101, 102 and 103, diodes 105, 106, 107 and 108 and resistor 110. The amplified and rectified voltage signal is supplied to negative ion output source 52 for adjustable negative ion output thereat and to platform surface 26.

The output from transformer 93 is connected to amplifier/rectifier circuitry 114. Amplifier and rectifier circuitry 114 includes capacitors 116 and 117 and diodes 119 and 120 in a conventional configuration, and is connected through resistor 122 to positive field collector 28. Variable resistor 90 enables user control over the intensity of the positive electrostatic field produced at the field collector in a range from 0 to +13 KV.

FIG. 5 is a block diagram illustrating another embodiment of a circuitry for apparatus 10. The unit is connected to a 110 volt AC power source and includes fuse 125 (for example a ¼ amp fuse) and on/off switch 127. The 110 volt AC signal is coupled through fuse 125 and switch 127 with the input of AC to DC converter and constant voltage regulator 129, for example a POWER-ONE, Inc. HB12-1.7A AC to DC converter and constant voltage regulator unit, which provides a −12 volt DC and a +12 volt DC signal at its outputs.

The negative signal output is connected to the input of voltage regulator and current limiter 131 for limiting the amperage at its two outputs to 150 ma with an output voltage of 6 to 12 volts, depending on the particular application.

Potentiometers 133 and 135 are provided to adjust voltage to thus allow a user of the apparatus control over the quantity of ions output by ion source 52 (in a range from 500 to 5,000,000 negative ions per cubic centimeter, with the ions being in the 0.001 micron range) and intensity of the negative charge at platform surface 26, respectively. The signals are then amplified by amplifiers 137 and 139 (for example Murata Erie Company 7700-694-000 amplifying units) and presented at current limiters 141 and 143 for limitation of current to 0.005 ma (as heretofore set forth) before coupling of the output signal to negative ion output source 52 and staging surface 26, respectively.

The positive signal from AC to DC converter and constant voltage regulator 129 may be provided at the input to optional pulse generator circuitry 145 which is connected to pulse frequency control circuit 147 for providing frequency controllable pulsations in the positive field at collector 26. The signal (from pulse frequency control circuit 147 when included, or from converter/regulator 129 when not) is provided at the input of voltage regulator and current limiter 149 for regulating the voltage at 6 or 12 volts, as desired, and limiting the current to 150 ma.

The signal at the output of voltage regulator and current limiter 149 is coupled with the input of potentiometer 151 to provide user control over the intensity of the positive electrostatic field in a range between 0 and 13 kilovolts at the output of amplifier 153 (amplifier 153 being, for example, a Murata Erie 7700-327-000 amplifier). Amplifier 153 is connected to current limiter 155 for limitation of the current to 0.005 ma. The output signal therefrom is then coupled with field collector 28.

As may be appreciated from the foregoing, this invention provides an improved apparatus and method for removal of matter from product surfaces, for example masks, wafer boards, filters, glass, metal, and the like, particularly in controlled process environments, which utilizes a surface charged at a selected intensity and a preselected polarity, an ion generator for generating a selected quantity of ions of the preselected polarity, and an electrostatic field generator having a collector for generating electrostatic field at selected intensity and having a polarity opposite the polarity of the charged surface and the ions to disbond and collect unwanted particulate matter from the surface of the product by commonly charging the product and the matter to aid disbonding and oppositely charging the collector to attach the thus disbonded matter.

What is claimed is:

1. An apparatus for promoting cleaness of a product comprising:
    voltage supply means connectable with a voltage source for selectively supplying voltage;
    a surface for receipt of the product thereon and connected with said voltage supply means so that said surface is chargeable to a selected intensity and a preselected polarity;
    ion producing means connected with said voltage supply means for generating a selected quantity of ions of said preselected polarity; and
    electrostatic field establishing means connected with said voltage supply means for generating an electrostatic field having a selected electrostatic field intensity and a polarity opposite said preselected polarity, said electrostatic field establishing means including a collector spaced from said surface.

2. The apparatus of claim 1 further comprising control means connected with said voltage supply means, said surface, said ion producing means and said electrostatic field establishing means for controlling said intensity of said charge at said surface and said quantity of said ions and said intensity of said electrostatic field.

3. The apparatus of claim 2 wherein said control means is connected so that said intensity of said charge at said surface and said quantity of ions are controlled simultaneously and independently from control of said intensity of said electrostatic field.

4. The apparatus of claim 1 wherein said ion producing means includes a selectively positionable electrode, said apparatus further comprising gas stream supply means having an outlet mounted adjacent to said electrode for providing a selectively directable gas stream having said ions therein.

5. The apparatus of claim 4 wherein said gas stream supply means includes control means for controlling direction and flow of said gas stream.

6. The apparatus of claim 1 further comprising mounting structure defining a product cleaning area and having said surface and said collector of said field establishing means mounted thereon.

7. The apparatus of claim 6 wherein said collector includes an arcuate surface defining one boundary of said cleaning area.

8. An apparatus for cleaning product surfaces comprising:
    voltage supply means connectable with a voltage source for selective supplying voltage;
    a first mounting structure for defining a product cleaning area;
    a second selectively movable mounting structure;
    a platform mounted on said first mounting structure of said cleaning area for receipt of the product thereon, said platform being connected with said voltage supply so that said platform is negatively chargeable to a selected intensity;
    negative ion producing means mounted on said second mounting structure and connected with said voltage supply means for generating a selected quantity of ions;
    a gas stream outlet positioned at said second mounting structure adjacent to said ion producing means and connectable with a source of pressurized gas; and
    electrostatic field establishing means connected with said voltage supply means for generating a positive electrostatic field having a selected electrostatic field intensity, said electrostatic field establishing means including a collector mounted on said mounting structure adjacent to said cleaning area.

9. The apparatus of claim 8 further comprising control means connected with said voltage supply means, said platform, said ion producing means and said electrostatic field establishing means for controlling said intensity of said charge at said platform, said quantity of ions and said intensity of said electrostatic field.

10. The apparatus of claim 9 wherein said electrostatic field intensity and said intensity of said charge at said platform are independently adjustable in a range of up to about 13 kilovolts.

11. The apparatus of claim 8 wherein said platform has a conductive surface onto which the product is placed.

12. The apparatus of claim 8 wherein said second mounting structure includes hand manipulable means for controlling direction and flow of said gas stream.

13. The apparatus of claim 8 further comprising filter means for filtering gas in said gas stream.

14. The apparatus of claim 8 wherein said collector includes an arcuate surface defining one boundary of said cleaning area.

15. A method for promoting cleanness of a product comprising the steps of:
- positioning said product on a surface;
- charging said surface to a selected intensity and a preselected polarity;
- generating a selected quantity of ions of the preselected polarity;
- directing said ions toward the product on said surface; and
- establishing at a collector spaced from said surface an electrostatic field having a selected intensity and a polarity opposite said preselected polarity.

16. The method of claim 1 further comprising the step of controlling said intensity of said charge at said surface, said quantity of ions, and said intensity of said electrostatic field.

17. The method of claim 15 wherein said charge at said surface is negative, said ions are negative, and said electrostatic field is positive.

18. The method of claim 15 further comprising the steps of generating a gas stream and directing said gas stream toward said surface.

19. The method of claim 18 including the step of filtering gas in said gas stream.

20. The method of claim 18 further comprising the step of selectively controlling the position of gas and ion generation relative to said surface.

* * * * *